(12) United States Patent
Whitebook et al.

(10) Patent No.: US 6,529,775 B2
(45) Date of Patent: Mar. 4, 2003

(54) SYSTEM AND METHOD EMPLOYING INDWELLING RF CATHETER FOR SYSTEMIC PATIENT WARMING BY APPLICATION OF DIELECTRIC HEATING

(75) Inventors: Mark Evan Whitebook, Capistrano Beach, CA (US); Blair D. Walker, Lake Forest, CA (US); Scott M. Evans, Santa Ana, CA (US); Lynn M. Shimada, Orange, CA (US)

(73) Assignee: Alsius Corporation, Irvine, CA (US)

(*) Notice: Subject to any disclaimer, the term of this patent is extended or adjusted under 35 U.S.C. 154(b) by 46 days.

(21) Appl. No.: 09/761,069

(22) Filed: Jan. 16, 2001

(65) Prior Publication Data

US 2002/0095198 A1 Jul. 18, 2002

(51) Int. Cl.$^7$ .................................................. A61F 2/00
(52) U.S. Cl. ...................... 607/101; 607/113; 607/99; 607/100
(58) Field of Search .................... 607/96–102, 104–106, 607/113; 606/27–29, 31

(56) References Cited

U.S. PATENT DOCUMENTS

| | | |
|---|---|---|
| 770,443 A | 9/1904 | Kinraide |
| 1,278,675 A | 9/1918 | Kawakita |
| 1,724,508 A | 8/1929 | Nauth |
| 1,733,763 A | 10/1929 | Werner |
| 2,008,526 A | 7/1935 | Wappler et al. |
| 2,032,859 A | 3/1936 | Wappler |
| 2,223,447 A | 12/1940 | Hathaway |
| 3,991,770 A | 11/1976 | LeVeen |
| 4,016,886 A | 4/1977 | Doss et al. |
| 4,119,102 A | 10/1978 | LeVeen |
| 4,154,246 A | 5/1979 | LeVeen |
| 4,160,455 A | 7/1979 | Law |
| 4,298,006 A | 11/1981 | Parks |
| 4,305,388 A | 12/1981 | Brisson |
| 4,312,364 A | 1/1982 | Convert et al. |
| 4,346,715 A | 8/1982 | Gammell |

(List continued on next page.)

FOREIGN PATENT DOCUMENTS

| | | |
|---|---|---|
| EP | 0 352 955 A2 | 1/1990 |
| EP | 0 428 875 A2 | 5/1991 |
| JP | 63-283638 | 11/1988 |
| SU | 0848031 | 10/1979 |
| WO | WO 84/02839 | 8/1984 |

OTHER PUBLICATIONS

U.S. patent application Ser. No. 09/282,971, Philips, pending.

U.S. patent application Ser. No. 09/390,600, Luo et al., pending.

(List continued on next page.)

Primary Examiner—Roy D. Gibson
(74) Attorney, Agent, or Firm—John L. Rogitz (57) ABSTRACT

An indwelling RF catheter achieves warming of patients by dielectric heating of blood or other bodily fluids. In one example, the catheter is deployed in a suitable blood vessel, such as the inferior vena cava. The catheter design includes an emitter structure electrically coupled to an RF generator, which provides a source of RF power. The emitter structure, distally located upon the catheter, administers electromagnetic radiation to the blood within the patient, thereby creating heat due to the dielectric qualities of blood. As blood heated by the indwelling RF catheter courses through the patient's body, the patient's body is systemically warmed, raising the body core temperature.

28 Claims, 6 Drawing Sheets

U.S. PATENT DOCUMENTS

| | | |
|---|---|---|
| 4,522,205 A | 6/1985 | Taylor et al. |
| RE32,057 E | 12/1985 | LeVeen |
| RE32,066 E | 1/1986 | LeVeen |
| 4,565,200 A | 1/1986 | Cosman |
| 4,638,436 A | 1/1987 | Badger et al. |
| 4,676,258 A | 6/1987 | Inokuchi et al. |
| 4,679,561 A | 7/1987 | Doss |
| 4,776,349 A | 10/1988 | Nashef et al. |
| 4,785,823 A * | 11/1988 | Eggers et al. ............... 600/374 |
| 4,821,725 A | 4/1989 | Azam et al. |
| 4,844,074 A | 7/1989 | Kurucz |
| 4,907,589 A | 3/1990 | Cosman |
| 4,920,978 A | 5/1990 | Colvin |
| 4,945,912 A | 8/1990 | Langberg |
| 5,019,075 A | 5/1991 | Spears et al. |
| 5,057,105 A | 10/1991 | Malone et al. |
| 5,092,841 A | 3/1992 | Spears |
| 5,098,429 A | 3/1992 | Sterzer |
| 5,106,360 A | 4/1992 | Ishiwara et al. |
| 5,122,137 A | 6/1992 | Lennox |
| 5,139,496 A | 8/1992 | Hed |
| 5,151,100 A | 9/1992 | Abele et al. |
| 5,160,828 A | 11/1992 | Olsen |
| 5,188,602 A | 2/1993 | Nichols |
| 5,191,883 A | 3/1993 | Lennox et al. |
| 5,211,631 A | 5/1993 | Scheaff |
| 5,279,598 A | 1/1994 | Sheaff |
| 5,304,214 A | 4/1994 | DeFord et al. |
| 5,346,508 A | 9/1994 | Hastings |
| 5,348,554 A | 9/1994 | Imran et al. |
| 5,433,740 A | 7/1995 | Yamaguchi |
| 5,486,208 A | 1/1996 | Ginsburg |
| 5,509,900 A | 4/1996 | Kirkman |
| 5,514,094 A | 5/1996 | Anello et al. |
| 5,542,928 A | 8/1996 | Evans et al. |
| 5,545,137 A | 8/1996 | Rudie et al. |
| 5,545,161 A | 8/1996 | Imran |
| 5,586,982 A | 12/1996 | Abela |
| 5,628,771 A | 5/1997 | Mizukawa et al. |
| 5,641,423 A | 6/1997 | Bridges et al. |
| 5,733,319 A | 3/1998 | Neilson et al. |
| 5,769,880 A | 6/1998 | Truckai et al. |
| 5,797,948 A | 8/1998 | Dunham |
| 5,800,493 A | 9/1998 | Stevens et al. |
| 5,837,003 A | 11/1998 | Ginsburg |
| 5,871,481 A | 2/1999 | Kannenberg et al. |
| 5,899,899 A | 5/1999 | Arless et al. |
| 5,919,187 A | 7/1999 | Guglielmi et al. |
| 5,925,038 A | 7/1999 | Panescu et al. |
| 5,975,081 A | 11/1999 | Hood et al. |
| 6,011,995 A | 1/2000 | Guglielmi et al. |
| 6,014,589 A | 1/2000 | Farley et al. |
| 6,019,783 A | 2/2000 | Philips et al. |
| 6,033,383 A | 3/2000 | Ginsburg |
| 6,071,263 A | 6/2000 | Kirkman |
| 6,071,277 A | 6/2000 | Farley et al. |
| 6,094,599 A | 7/2000 | Bingham et al. |
| 6,110,168 A | 8/2000 | Ginsburg |
| 6,146,411 A | 11/2000 | Noda et al. |
| 6,179,835 B1 * | 1/2001 | Panescu et al. ............. 600/374 |
| 6,190,356 B1 | 2/2001 | Bersin |
| 6,293,943 B1 * | 9/2001 | Panescu et al. ............... 606/27 |

OTHER PUBLICATIONS

U.S. patent application Ser. No. 09/396,200, Balding, pending.

U.S. patent application Ser. No. 09/413,752, Evans et al., pending.

U.S. patent application Ser. No. 09/413,753, Evans et al., pending.

U.S. patent application Ser. No. 09/427,745, Pham et al., pending.

U.S. patent application Ser. No. 09/477,490, Lasersohn et al., pending.

U.S. patent application Ser. No. 09/761,069, Whitebook et al., pending.

U.S. patent application Ser. No. 09/494,896, Philips et al., pending.

U.S. patent application Ser. No. 09/498,499, Worthen, pending.

U.S. patent application Ser. No. 09/546,814, Gobin et al., pending.

Bernard, S., Induced Hypothermia in Intensive Care Medicine, *Anaesth, Intensive Care*, Jun. 1996, 24(3):382–388.

Gillinov et al., Superior Cerebral Protection With Profound Hypothermia During Circulatory Arrest, *Annals of Thoracic Surgery*, Jun. 1993, 55(6):1432–1439.

Ginsberg et al., Therapeutic Modulation of Brain Temperature: Relevance to Ischemic Brain Injury, *Cerebrovascular and Brain Metabolism Reviews*, 1992 Fall, 4(3):189–225.

Maher et al., Hypothermia as a potential treatment for a cerebral ischemia, *Cerebrovascular and Brain Metabolism Reviews*, 1993 Winter, 5(4):277–300.

Marion et al., Resuscitative hypothermia, *Critical Care Medicine*, Feb. 1996, 24(2):S81–S89.

Marion et al., Treatment of traumatic brain injury with moderate hypothermia, *The New England Journal of Medicine*, Feb. 1997, 336(8):540–546.

Smirnov, O.A., New Method for Cooling (or Heating) the Body and an Apparatus for Craniocerebral Hypothermia, *Biomed Eng*, 1968 Nov.–Dec., 2(6):334–337.

* cited by examiner

SYSTEM AND METHOD EMPLOYING INDWELLING RF CATHETER FOR SYSTEMIC PATIENT WARMING BY APPLICATION OF DIELECTRIC HEATING

BACKGROUND OF THE INVENTION

1. Field of the Invention

The present invention relates to patient warming systems to prevent and treat hypothermia, especially for surgical or other hospital patients.

2. Description of the Related Art

It is common for certain medical patients to experience mild to severe hypothermia. Some examples include trauma patients, people with a compromised circulatory system, and patients under anesthesia. There are several causes for this decrease of body temperature. First, anesthesia depresses the body's metabolic rate, meaning that the body burns calories at a reduced rate, and therefore generates less heat. Second, anesthesia may have the effect of depressing the body's set-point temperature as regulated by the brain's thermal control center. Third, in a surgical procedure, the patient may have his or her thoracic or abdominal cavities opened, greatly increasing the amount of surface area exposed to the atmosphere as compared to normal, and thereby generating higher body-heat losses from convection and evaporation. Surgical heat loss is further complicated by the cool temperature of many surgical suites.

Current methods of treating hypothermic patients include heating blankets, which use air or liquid as the heat-transfer medium. If placed beneath the patient, heating blanket transfer thermal energy to the patient by a combination of conduction (by direct skin contact with the patient) and convection (via the local air film between the blanket surface and the patient's skin). Air-type heating blankets are typically placed over the patient, and supply warmed air under low pressure to the blanket, which in turn "leaks" the warmed air out at low velocity and with reasonable uniformity over its surface. In both cases, the thermal energy exchange must take place through the patient's skin surface, relying principally on the vascular system to transfer the thermal energy to the patient's "core" via blood flow.

The rate of heat transfer, and therefore the effectiveness, of a heat-blanket warming system is necessarily limited for various reasons. One reason is the body's natural response of "shutting down" blood flow to the extremities in the case of low core temperature. In addition to the problem of blood circulation to the extremities being reduced under conditions of hypothermia there are corollary issues to heating blanket methods, as well. One is the necessarily low power density (i.e., watts per unit area) that can be applied without damaging the skin and without eliciting a "sweat response," which would counter the intended heat input by sweat evaporation. Another inherent limitation is the physical remoteness of the applied heat from the critical core location. Warm air directed to the arms and legs, for instance, encounters a long series of barriers between the point of applied thermal energy and the core. Thermal energy must first warm the epidermis by convection, then warm the underlying skin layers by conduction. From the underlying skin layers, the thermal energy must be conducted to muscle tissue, and then eventually to the small vessels of the circulatory system (which, as noted, may be constricted as a response to the body's hypothermic condition).

Physicians also employ intravenous (IV) fluid warmers as another technique for treating hypothermic patients. These devices serve to heat IV solutions that are infused into the patient during surgical procedures. Because of the limitations of volume that can be infused into a patient during typical procedures, these devices lack the capacity to quickly rewarm patients with depressed body temperature.

Consequently, known patient warming approaches are not completely adequate for all applications due to certain unsolved problems.

SUMMARY OF THE INVENTION

Broadly, this invention concerns an indwelling radio frequency (RF) catheter that systemically warms patients by dielectric heating of bodily fluids. Although blood is used as a representative example, other bodily fluids are contemplated, such as cerebral spinal fluid. The blood is heated "in vivo," meaning "within the body." The indwelling catheter is deployed in a suitable blood vessel, such as the inferior vena cava. The catheter design includes a distally positioned emitter structure electrically coupled to a remote RF generator, which provides a source of RF power. The emitter structure applies a controlled, high-frequency electric field to blood within the patient, thereby creating heat due to the dielectric loss properties of the blood, due in turn to its water content. Advantageously, the emitter may include a bipolar electrode structure, where both poles are present in the patient's body cavity. Another option is a unipolar emitter structure, which relies upon electric flow between the emitter and the patient's body. Heating by the indwelling RF catheter continues for a sufficient time that the patient is systemically warmed as blood courses through the patient's body under influence of the patient's own circulatory system and/or artificial circulation-aiding machines. The invention may also include various protective or self-distancing structures to prevent the emitter from contacting the surrounding bodily cavity.

The foregoing features may be implemented in a number of different forms. For example, the invention may be implemented to provide a method of increasing a patient's core temperature by dielectric warming of bodily fluids. In another embodiment, the invention may be implemented to provide an apparatus such as a catheter and/or patient warming system with suitable structure to perform dielectric warming of blood.

The invention affords its users with a number of distinct advantages. For example, the protective and self-distancing features of the invention address the problem of warming a patient at risk for hypothermia without creating clinically significant localized hot spots capable of damaging tissue or blood by protein denaturation. Moreover, this invention provides a greater level of warming beyond that of current thermal-assist technologies, such as externally applied conductive or convective methods. Still another advantage is that the invention applies its heat load nearly directly at the body's core, where it is most needed in hypothermia. The invention also provides a number of other advantages and benefits, which should be apparent from the following description of the invention.

DETAILED DESCRIPTION

The nature, objectives, and advantages of the invention will become more apparent to those skilled in the art after considering the following detailed description in connection with the accompanying drawings.

HARDWARE COMPONENTS & INTERCONNECTIONS

Introduction

Figure 1:
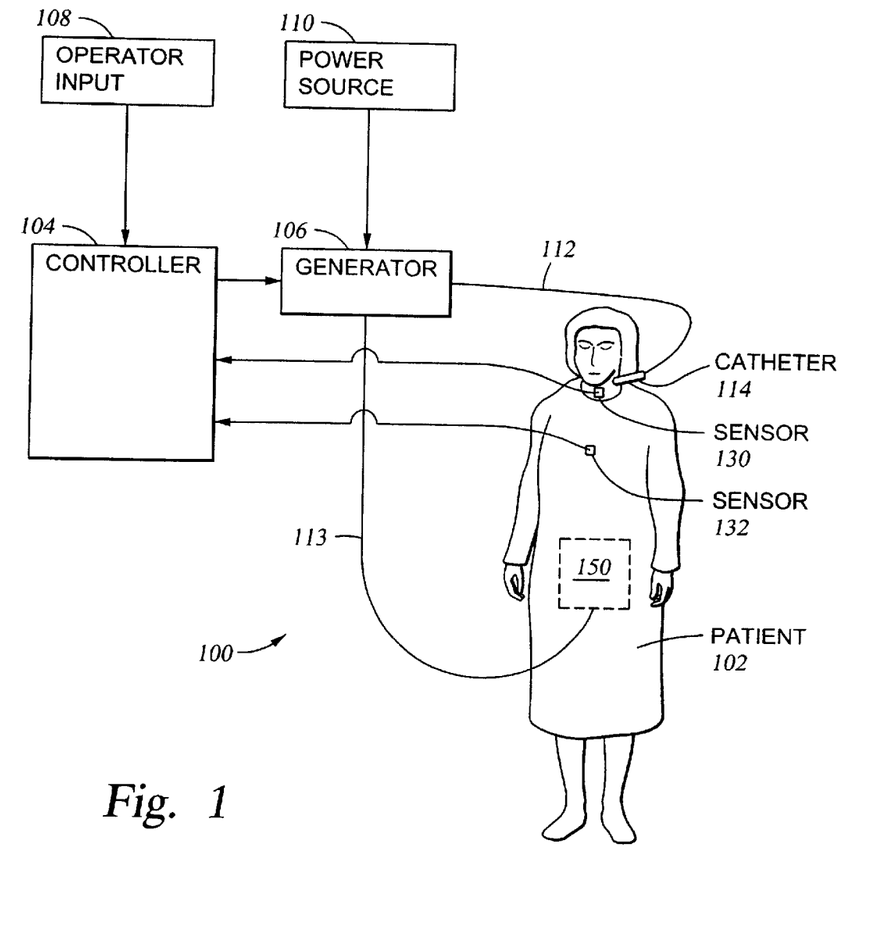
FIG. 1 is a block diagram of the hardware components and interconnections of a patient warming system according to this invention.

One aspect of the invention concerns a system to treat or prevent hypothermia in hospital patients by performing dielectric heating of bodily fluids with a water component, such as blood, cerebral spinal fluid, etc. Aside from addressing hypothermia, the invention may also be used to warm bodily fluids for other purposes as well, such as localized heating of an organ, etc. This system may be implemented in various ways, one example being shown by the hardware components and interconnections of the system 100 (FIG. 1). The system 100 includes a controller 104, generator 106, one or more temperature sensors 130, 132, an operator input 108, power source 110, catheter 114, and link 112. Optionally, a conductive grounding plate 150 may be attached to the patient's skin at a site that provides sufficient conduction, such as the patient's back or buttocks. The plate 150 is coupled to the generator 106 by a return link 113. As described below, the system 100 may be utilized to automatically treat or even prevent hypothermia in the patient 102.

Catheter

Broadly, the catheter 114 comprises an elongated member shaped for insertion into canals, vessels, veins, passageways, or other bodily cavities. The catheter 114 may have a tube shape, for example. The catheter includes a distally positioned emitter that emits electromagnetic radiation, which heats nearby blood under the principle of dielectric heating. As discussed in greater detail below, one example of such electromagnetic radiation is radio frequency (RF) energy. The catheter 114 receives its RF or other electrical signal from the generator 106.

This signal is received over a link 112. In the case of a bipolar electrode catheter (discussed below), the link 112 supplies input current to the catheter 114 and also receives return current from the catheter 114. In the case of a unipolar electrode catheter (discussed below), the link 114 supplies only input current to the catheter 114. Return current is received from the patient's body at the conductive grounding plate 150 and returned to the generator 106 via the return link 113.

In the case of bipolar electrode catheters, the link 112 comprises a multi-conductor member. In the case of unipolar electrode catheters, the link 112 comprises a single-conductor member. In either case, the links 112, 113 may be provided by wire, cable, or other conductive product. For use in higher frequencies, the links 112, 113 may be advantageously constructed of coaxial cable. For coaxial cable in this application, desirable features include small cross-sectional size, significant flexibility, biocompatibility, efficient power transmission (i.e., low power loss), and impedance that matches both the source impedance of the generator 106 and the load impedance of the catheter 114. At lower frequencies, the links 112, 113 may be implemented by stranded wires.

If desired, the catheter 114 may incorporate a sensor 130, consolidating the otherwise separate tasks of installing the catheter 114 and sensor 130. The functions of the sensor 130 are discussed in greater detail below. The sensor 130 may be attached to a proximal, distal, or other location of the catheter by adhesive bonding, mechanical attachment, or other flexible tether in order to yield some separation between the sensor 130 and the emitter and avoid impinging RF energy from the emitter to the sensor 130 and possibly distorting the sensor's reading.

Generator

As mentioned above, the catheter 114 receives electrical signals from the generator 106. The generator 106 converts electricit; from a principal source of one-hundred-ten volt or other power (e.g., wall plug, storage batteries, primary batteries, etc.) into alternating current power having a desired frequency. As an example, the generator 106 may include an oscillator, intermediate power stage, and final power stage. The oscillator determines the oscillating frequency, and may be implemented as a crystal oscillator, L-C oscillator circuit, IC oscillator, etc. The intermediate power stage boosts the oscillator's output to a power level adequate to drive the final power stage. The final power stage provides high power output at the oscillator's frequency sufficient to drive the catheter's emitter at a desired level.

Depending upon the needs of the application, the generator 106 may be implemented to RF energy with fixed electrical properties, one or more properties, or alternatively vary in accordance with input from the controller 104. The generator 106 may be implemented by a machine such as a solid state power amplifier ("SSPA"), traveling wave tube amplifier ("TWTA"), Klystron amplifier, or other suitable apparatus.

In the present example, the electromagnetic energy of the generator 106 comprises RF power. In this example, the generator 106 provides output signals, whether fixed or variable frequency, in the range from 13 MHz to 27.12 MHz. This band corresponds to the Instrumentation, Scientific, and Medical (ISM) bands presently dedicated by the Federal Communications Commission (FCC) for medical applications such as diathermy.

Alternatively, under a different administrative regulation, the generator may operate in the range from 915 MHz to 2.45 GHz. Apart from administrative concerns, the frequency range may be established appropriately to meet concerns with safety, efficacy, power efficiency, and the like. For instance, the operating frequency depends in part on the relative dielectric loss of the target material (blood) as a function of frequency, as well practical engineering considerations, such as the difficulty of generating and delivering clinically useful levels of power. Thus, ordinarily skilled artisans (having the benefit of this disclosure) may recognize other useful frequency ranges nonetheless contemplated by this invention.

The generator 106 may utilize amplitude modulation, duty cycle modulation frequency modulation, or another useful modulation scheme.

Sensors

If desired, the system 100 may include one or more sensors, such as the illustrated sensors 130, 132. The sensor 130 is installed in the bodily passage where the catheter 114 is deployed, and serves to detect the temperature of blood in the immediate heating area of the catheter 114. Another sensor 132 may be deployed in the patient 102, at one of many sites known to be accurate for measuring body core temperature. Some examples include esophageal, bladder, rectal, tympanic (eardrum) or oral installation. Alternatively, instead of sensing temperature directly, the sensor 132 may detect another physiological characteristic that is nonetheless indicative of body temperature, such as metabolic rate.

Controller—Generally

The controller 104 receives machine-readable measurements from the sensor(s) 130, 132, and also receives inputs from an operator input source 108. The operator input source 108 may comprise as a keyboard, computer mouse, voice sensor, dial/switch panel, foot pedal, touch input screen, digitizing pen, or other human-machine interface. In accordance with input from the source 108 and sensors 130, 132, the controller 104 regulates the operation of the generator 106 by adjusting the generator's frequency, duty cycle, on/off times, power, or other electrical characteristics of the generator's output. The details of the controller's operation, which are dictated by its software code, circuit layout, and/or programming, are discussed below in relation to FIG. 8.

In order to implement the controller's automatic control capability, the controller 104 may utilize electronic structure such as logic circuitry, discrete circuit elements, or a digital data processing apparatus (computer) that executes a program of machine-readable instructions. When implemented in logic circuitry or a computer, the controller 104 utilizes its own programming to analyze the temperature of the patient 102 and/or blood in the body cavity where the catheter is deployed, and provide the resultant output signal to regulate the generator 106. When implemented in discrete circuitry, the circuitry of the controller 104 processes the sensed temperature(s) to provide a resultant output signal that regulates the generator 106.

Controller—Digital Data Processing Apparatus

As mentioned above, one embodiment of the controller 104 is a digital data processing apparatus. This apparatus may be embodied by various hardware components and interconnections, one example appearing in FIG. 6. The apparatus 600 includes a processor 602, such as a microprocessor or other processing machine, coupled to a storage 604. In the present example, the storage 604 includes a fast-access storage 606, as well as nonvolatile storage 608. The fast-access storage 606 may comprise random access memory (RAM), and may be used to store the programming instructions executed by the processor 602. The nonvolatile storage 608 may comprise, for example, one or more magnetic data storage disks such as a "hard drive", a tape drive, or any other suitable storage device. The apparatus 600 also includes an input/output 610, such as a line, bus, cable, electromagnetic link, or ocher means for the processor 602 to exchange data with other hardware external to the apparatus 600.

Despite the specific foregoing description, ordinarily skilled artisans (having the benefit of this disclosure) will recognize that the apparatus discussed above may be implemented in a machine of different construction, without departing from the scope of the invention. As a specific example, one of the components 606, 608 may be eliminated; furthermore, the storage 604 may be provided on-board the processor 602, or even provided externally to the apparatus 600.

Controller—Loglic Circuitry

In contrast to the digital data storage apparatus discussed previously, a different embodiment of the invention implements the controller 104 with logic circuitry instead of computer-executed instructions. Depending upon the particular requirements of the application in the areas of speed, expense, tooling costs, and the like, this logic may be implemented by constructing an application-specific integrated circuit (ASIC) having thousands of tiny integrated transistors. Such an ASIC may be implemented using CMOS, TTL, VLSI, or another suitable construction. Other alternatives include a digital signal processing chip (DSP), discrete circuitry (such as resistors, capacitors, diodes, inductors, and transistors), field programmable gate array (FPGA), programmable logic array (PLA), and the like.

Emitter

As mentioned above, the catheter 114 includes an electrical energy dissipating structure called an "emitter" to dispense electromagnetic radiation. The emitter acts as an antenna, imparting RF energy into blood or other bodily fluid that is present in the bodily cavity where the catheter 114 is deployed. Generally, the emitter has a narrow, elongated, tube shape to facilitate deployment in elongated bodily passages such as veins, blood vessels, etc. The emitter, which resides at the distal end of the catheter 114, may take various forms as shown below.

The emitter is structured to create a local electric field such that the optimum volume of blood or other bodily fluid is subject to the emitter's RF field while minimizing the warming of surrounding tissue. In implementations shown in FIGS. 2–5 as discussed below, the emitter creates a substantially circularly symmetric field about its axis with reasonable uniformity along its active length, describing a cylindrical field distribution. In such an implementation, the electric field amplitude decreases with inverse proportionality to the distance from the emitter's axis. The power of the field, which is proportional to the square of its amplitude, therefore decreases as the inverse square of the radial distance from the emitter. Hence, an incremental volume of blood two millimeters from the emitter will experience a power loading that is one-fourth that of an identical incremental volume one millimeter from the emitter. Thus, the effective heating power of the coaxial field design becomes progressively lower approaching the outer cylindrical electrode, helping to confine the heating effect to the flowing blood, and diminishing the threat of overheating adjacent fixed-position body structures.

Figure 2:
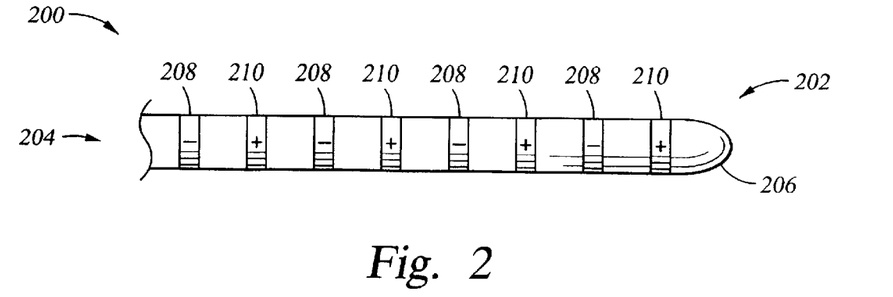
FIG. 2 is a plan view of an alternating bipolar emitter structure, according to the invention.

FIGS. 2–5 describe a variety of different exemplary emitter structures. Referring to FIG. 2, a bipolar, alternating electrode structure is shown. The emitter of FIG. 2 provides an example of a "flow-around" emitter, since blood is warmed as it flows around the emitter. The emitter 200 includes an emitter body 206 having distal 202 and proximal 204 ends. The catheter body 206 is made from a non-conductive material such as plastic, glass, ceramic, etc. The body 206 incorporates a number of electrodes made from electrically conductive materials. In a bipolar design (as shown), the electrodes include those which are negative 208 at a given instant and those which are positive 210 in that same instant. This assignment of polarity is not fixed, and the electrodes (poles) exchange their relative state many times per second according to the RF frequency of the power source. The positive and negative electrode assignment is illustrated only to help delineate the instantaneously opposed nature of the electrodes. The electrodes may be manufactured from an electrically conductive, biocompatible material designed to directly contact blood or other bodily fluids that immerse the emitter 200, or a non-biocompatible material that is shielded from patient contact by a suitable impermeable layer such as a dielectric insulator. An example of a conductive, biocompatible material is stainless steel or a gold-plated metal such as aluminum, copper, nickel, etc. An example of a non-metallic conductor is p-type or n-type silicon.

The electrodes 208,210 may be formed by discrete components, such as stainless-steel rings, plates, tubes, etc. Such components may be fastened by mechanical means, such as crimping, swaging, shrinking, adhesive bonding with a biologically-compatible glue, etc. Alternatively, the electrodes may be applied as thin or thick films to a non-conductive dielectric substrate by plating, electrodeposition, sputtering, evaporation, silk-screening, etc. Intervening regions of the emitter body 206 serve to electrically separate the electrodes 208, 210 from each other. In the example of FIG. 2, the electrodes 208, 210 comprise alternating rings encircling a cylindrical catheter body 206. The rings are laid out side-by-side since they are distributed along the longitude of the emitter body 206. Nonetheless, as shown by some examples below, the electrodes may be arranged as parallel plates, parallel wires, interdigitated fingers, or alternating rings on a cylindrical, elliptical, or rectangular dielectric substrate.

Figure 3:
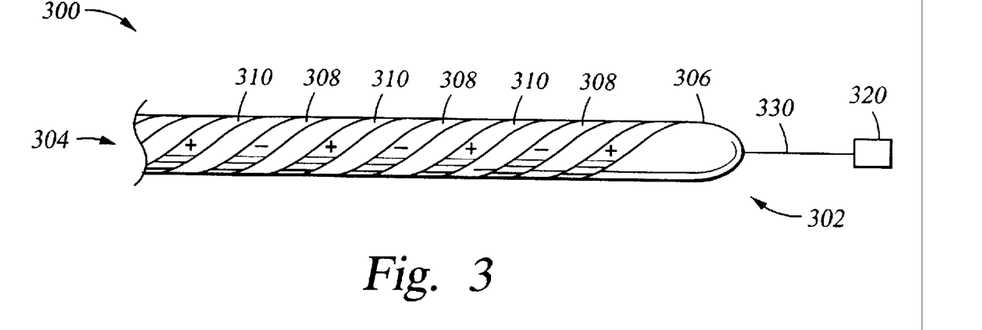
FIG. 3 is a plan view of a spiraling bipolar emitter structure, according to the invention.

FIG. 3 shows a different example of bipolar electrode structure, with spiraling electrodes. The emitter of FIG. 3 also provides an example of a "flow-around" emitter, since blood is warmed as it flows around the emitter. The emitter 300 includes an emitter body 306 having distal 302 and proximal 304 ends. The body 306 incorporates a number of electrodes 308,310, which comprise continuous, interlaced spirals that encircle the body 306.

This specific illustration of emitter 300 is also used to demonstrate the possible addition of a sensor 320 to the emitter. The sensor 320 may serve as the on-site sensor 130. The sensor 320 senses temperature or another bodily property indicative of metabolic condition. The sensor 320 is coupled to the emitter's distal end 302 by a tether 330, which enables the sensor 320 to assume a position away from the emitter body 306. For example, under influence of blood flow in a blood vessel, the sensor 320 may naturally position itself downstream from the emitter body 306. Separation from the emitter 306 helps the sensor 320 avoid erroneous temperature measurements under influence from the emitter's electric field. Although the sensor 320 is illustrated in FIG. 3, this sensor 320 may be similarly implemented in the embodiments of FIGS. 2, 4A–4H, and 5. Also, the sensor 320 may be attached to the catheter body itself, separated by distance or insulated with some material from the poles 310, 308 rather than being tethered.

Figure 4A:
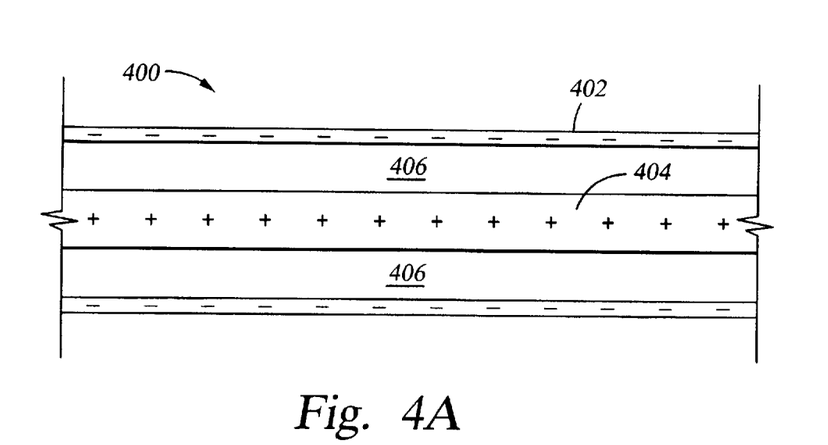
FIG. 4A a cutaway plan view of a coaxial bipolar emitter structure, according to the invention.
Figure 4B:
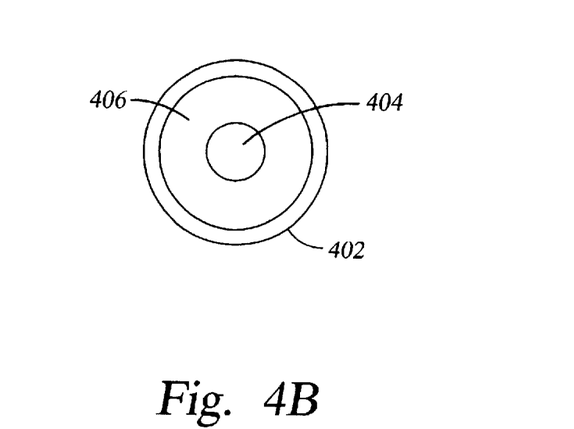
FIG. 4B a cross-sectional end view of the coaxial bipolar emitter structure of FIG. 4A, according to the invention.

FIGS. 4A–4B show a different example of bipolar emitter, which uses a concentric electrode structure. The emitter of FIGS. 4A–4B is an example of a "flow-through" emitter, since blood is warmed as it flows through the emitter. The emitter 400 includes an inner electrode 404 and an outer electrode 402. The electrodes 404, 402 are shown as positive and negative, respectively, although their polarity may change frequently according to the modulation scheme. The interstitial, annular space 406 between the electrodes 402, 404 permits blood to flow along the longitudinal axis of the emitter 400. Regarding the outer cylindrical electrode 402 of the illustrated coaxial bipolar construction, this electrode is attached to and separated from the main catheter body 404 by non-conductive "spacers" (not shown) such as struts, rods, vanes, spokes, filaments, etc. radiating from the central body of the catheter. These spacers are configured so as to positively center the two structures for uniform field distribution, while allowing the free flow of blood through the annular space.

Figure 5:
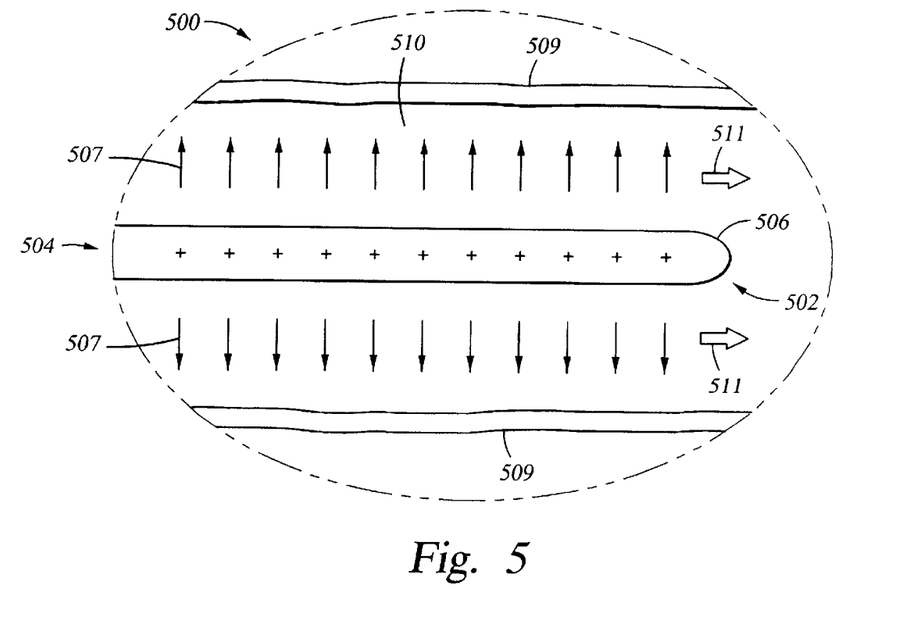
FIG. 5 a cutaway side view of a blood vessel wall also showing a unipolar catheter structure in plan view, according to the invention.

FIG. 5 shows an example of unipolar electrode structure in contrast to the bipolar structures of FIGS. 2–4B. The emitter of FIG. 5 is an example of al "flow-around" emitter, since blood can flow around the catheter 500 via the space 510 between the catheter 510 and the surrounding vessel wall 509. The emitter 500 includes a catheter body 506 having distal 502 and proximal 504 ends. The body 506 serves as one electrode (electrically positive in the illustrated instant), with the patient's body 509 providing an electrical path back to the conductive grounding plate 150 (serving as the negative pole in the illustrated instant). The catheter's field is shown by 507. The catheter body 506 may be constructed of an elongated member that is made of a conductive material or includes a conductive layer or coating. Blood flows around the emitter body 506 in the channel 510 formed between the emitter body 506 and the blood vessel wall 509, as shown by the flow direction arrows 511.

Emitter Non-Contact Features

The emitter may include various features to help keep the emitter from contacting walls of a blood vessel or bodily cavity where the emitter is deployed. This may be desirable from the standpoint of preventing necrosis of tissue lining the vessel where the emitter is deployed.

Figure 4C:
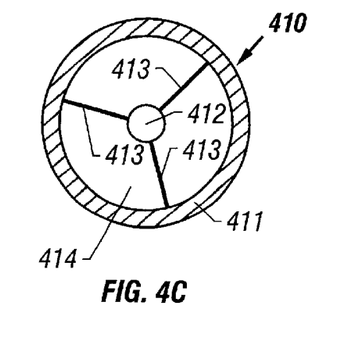
FIG. 4C is a cross-sectional end view of a collapsible coaxial emitter protective structure in uncollapsed form, according to the invention.
Figure 4D:
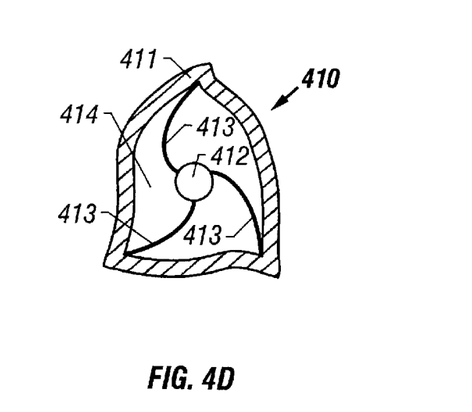
FIG. 4D is a cross-sectional end view of the collapsible coaxial emitter protective structure of FIG. 4C in collapsed form, according to the invention.
Figure 4E:
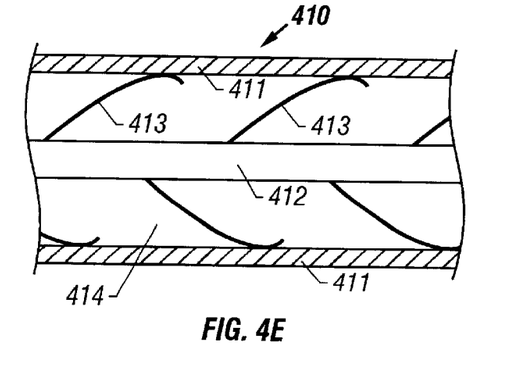
FIG. 4E is a cutaway side plan view of the collapsible emitter protective structure of FIG. 4C in uncollapsed from, according to the invention.

One such feature is embodied by the structure of FIGS. 4C–4E, which depict a collapsible emitter protective structure 410. The structure 410 includes an emitter 412, such as one of the emitters discussed above. The emitter is centrally disposed within an outer sheath 411, which comprises a material with properties of flexibility so that it can collapse as shown in FIG. 4D and also biocompatibility to allow longer term use in the blood stream. Some exemplary materials include polyoletias, nylon, PVC, flexible coated or uncoated metals, etc. The distance between the emitter 412 and the outer sheath 411 is maintained by multiple spacers 413, made from a resilient, biocompatible material such as metal wire, shape memory metal such as Nitinol, plastic, etc. The spacers 413 are attached to the emitter 412 by means of adhesive, mechanical attachment, soldering, etc. Spacers 413 protrude from different radial directions of the emitter 412, and they are distributed longitudinally along the emitter 412. Optionally, the spacers 413 may be of equal length to aid in spacing the emitter 412 similar distances from the surrounding walls of a blood vessel or other bodily cavity.

Attachment of the spacers 413 to the sheath 411 may be achieved by similar means, or omitted entirely in which case the sheath 411 may be slid over the emitter 412 and spacers 413 before use, and removed and discarded after use. As illustrated, the spacers are attached to the emitter 412 at acute angles, to permit collapse of the sheath 411 by depressing distal ends of the spacers 413 toward the emitter 412. FIG. 4D depicts the structure 410 in collapsed form. Collapsing of the structure 410 allows easier insertion through smaller entrance incisions, puncture wounds, etc. After insertion, the structure 410 expands to create a flow channel for bodily fluids in the space 414. If desired, the structure 410 may incorporate the concentric bipolar electrode structure of FIGS. 4A–4B, where the outer sheath 411 provides one electrode and the central member 412 provides the opposite polarity electrode.

Figure 4F:
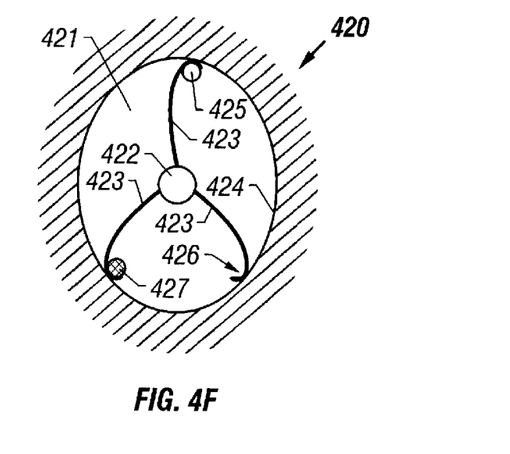
FIG. 4F is a cross sectional end view of a free-end self-distancing emitter structure, according to the invention.
Figure 4G:
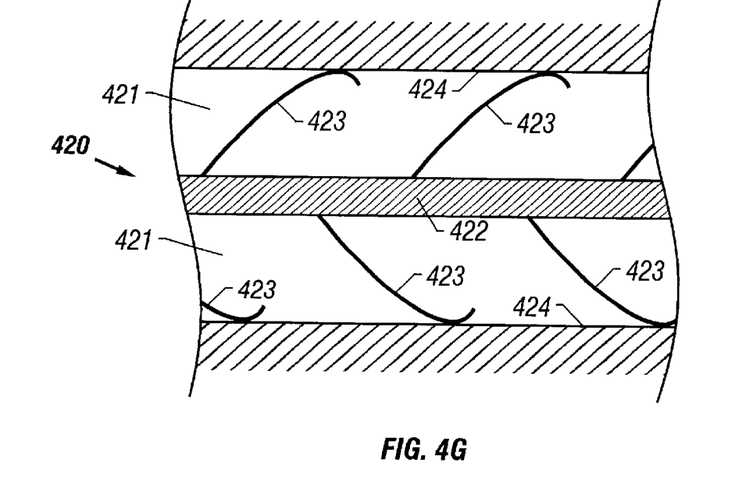
FIG. 4G is a cutaway side plan view of the free-nd self-distancing emitter structure as deployed in a bodily cavity, according to the invention.

FIG. 4F depicts another feature to help keep an emitter from contacting walls of a blood vessel or bodily cavity where the emitter is deployed. Namely, FIG. 4F depicts a free-end self-distancing emitter structure 420. The structure 420 includes an emitter 422, such as one of the emitters discussed above. The emitter 422 is attached to spacers 423, as with the foregoing embodiment of FIGS. 4C–4E. However, the spacers 423 are free-end since there is no outer sheath. FIG. 4F depicts the structure 420 deployed within a bodily cavity 421, the spacers 423 being slightly bent against the cavity wall 424, thereby urging the emitter 422 toward the center of the cavity 421. Thus, the structure 420 is self-distancing with respect to the cavity walls 424. To avoid injuring the cavity walls 424, the ends of the spacers 423 may be curved (such as 426), wound into a circle (such as 425), or attached to a protective mechanism such as a pad or ball (such as 427), or other atraumatic device. FIG. 4G shows the structure 420 in side view, deployed within the bodily cavity 421, devices 425–427 being omitted for greater clarity of illustration.

Figure 4H:
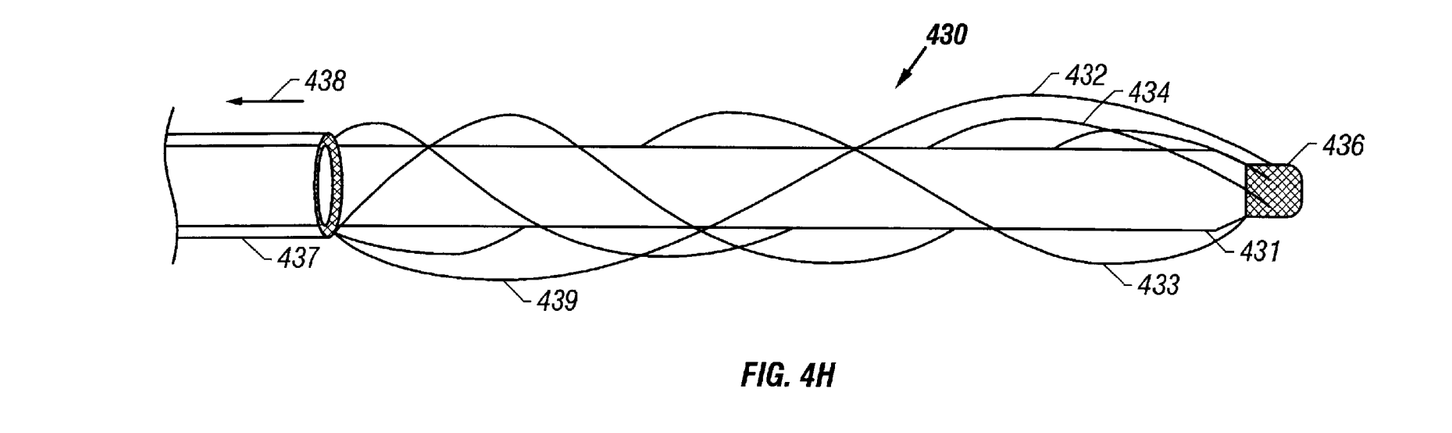
FIG. 4H is a side plan view of a distally attached remotely actuated self-distancing emitter structure, according to the invention.

FIG. 4H shows a different structure to keep the emitter from contacting walls of a blood vessel or bodily cavity where the emitter is deployed. Namely, the structure 430 exemplifies a remotely actuated self-distancing emitter structure, which may also be referred to as a "stone basket" type device. The structure 430 includes an emitter 431, such as one of the emitters discussed above. The emitter 431 is attached to multiple spacers (e.g., 432–434), which each constitute a resilient, biocompatible material such as metal shape memory wire, Nitinol, plastic, etc. Each spacer is distally attached to the emitter 431 at a connecting point 436, and proximally attached to a movable outer sleeve 437. Attachment may be achieved, for example, by means of soldering, adhesive, etc. Some spacers may spirally wrap around the emitter 431 in left-hand fashion, other spacers wrapping in right-hand fashion, and still others passing directly along the emitter's length without any spiral component.

The outer sleeve 437 comprises a generally cylindrical attachment point for the spacers, and surrounds the emitter 431 with appropriate looseness to permit longitudinal movement of the sleeve 437 along the emitter. The sleeve may be actuated by pulling or pushing the sleeve itself where the sleeve is sufficiently long to extend out of the body), pulling or pushing a line (such as a wire) to remotely actuate the sleeve, etc. In another embodiment, the sleeve 437 may encase a spring wound about the emitter body 431 but inside the sleeve, which urges the sleeve 437 toward the distal end 436, thereby automatically activating the sleeve 437. During installation into the body, medical staff keep the structure 430 in a collapsed configuration by maintaining tension on a wire attached to the sleeve to pull it in a direction 438 away from the distal end 436.

When the sleeve is appropriately actuated by one of the foregoing means, self-distancing is provided because the curved, protruding bight of each spacer between its respective ends (such as the portion 439 of the spacer 432), provides an elastic cushion that resiliently urges the emitter 431 away from any object that contacts the bight 439. With so many spacers providing bights radially disposed about the emitter 431, the spacers serve to position the emitter 431 centrally within a bodily cavity, preventing contact between the emitter 431 and any cavity walls.

Figure 4I:
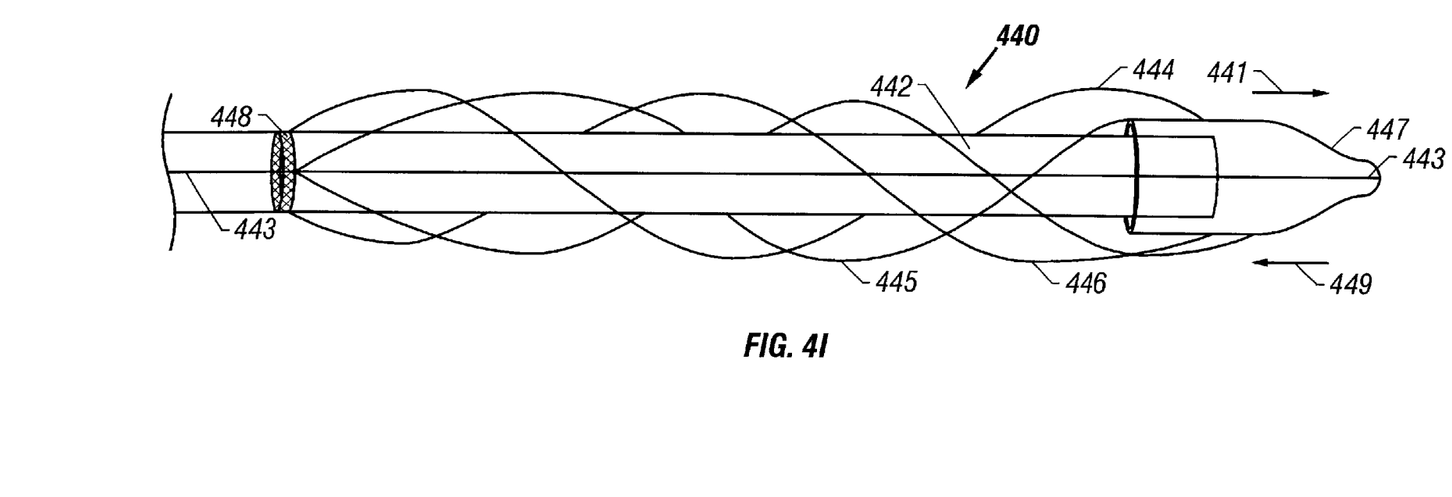
FIG. 4I is a side plan view of a proximally attached remotely actuated self-distancing emitter structure, according to the invention.

FIG. 4I shows a different embodiment of remotely actuated self-distancing emitter structure. The structure 440 utilizes an emitter 442, such as one of the emitters discussed above. The emitter is attached to multiple spacers (e.g. 444–446), comprising similar materials as discussed above. Each spacer 444–446 is proximally attached to the emitter 442 at a fixed connecting point 448, and distally attached to a movable tip section 447. The spacers may spirally wrap about the emitter 442 in right or left-hand fashion, pass longitudinally without and wrapping, or a mix of these.

The tip 447 comprises a cap over the emitter's distal end that is normally biased in a direction 441 (to keep the spacers straight) by a resilient member such as a spring between the tip 447 and emitter 442, elastomeric layer, etc. Attentively, the tip 447 may be held in a distal position (preventing ant bight in the spacers 444–446) by there being a snug fit about the emitter 442. The tip 447 is actuated by pulling an inner retractor 443, which is connected to the tip 447, and thus urges the tip 447 in a direction 449. The retractor 443 comprises a wire or probe, for example.

OPERATION

In addition to the structure described above, a different aspect of the invention concerns a process for systemic patient warming by using an indwelling RF catheter to locally warm bodily fluids in the patient's circulatory system. As illustrated below, this process includes some steps that are manually performed, and some automatic, machine-activated steps.

Signal-Bearing Medium

Figure 6:
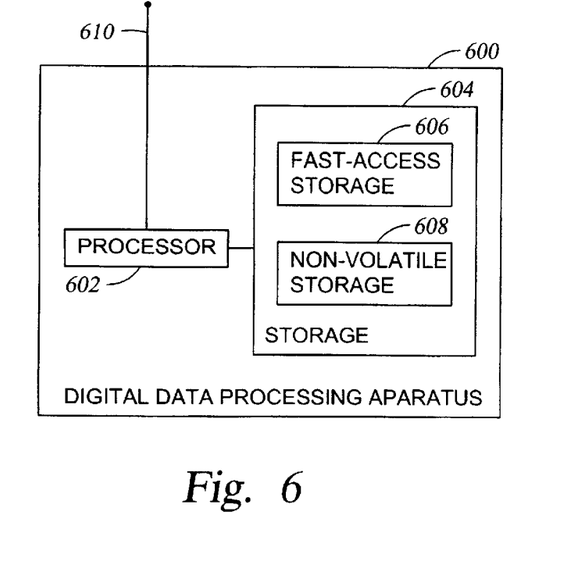
FIG. 6 is a block diagram of a digital data processing machine according to the invention.

The patient warming system may be implemented, for example, by operating the controller 104, as embodied by a digital data processing apparatus 600, to execute a sequence of machine-readable instructions. These instructions may reside in various types of signal-bearing media. In this respect, one aspect of the present invention concerns a programmed product, comprising signal-bearing media tangibly embodying a program of machine-readable instructions executable by a digital data processor to operate the system 100 to perform automated patient warming.

Figure 7:
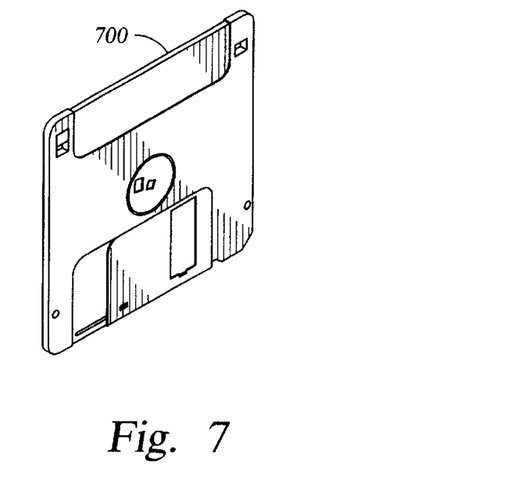
FIG. 7 shows an exemplary signal-bearing medium according to the invention.

This signal-bearing media may comprise, for example, RAM (not shown) contained within the controller 104, as represented by the fast-access storage 606, for example. Alternatively, the instructions may be contained in another signal-bearing media, such as a magnetic data storage diskette 700 (FIG. 7), directly or indirectly accessible by the processor 602. Whether contained in the diskette 700, storage 604, or elsewhere, the instructions may be stored on a variety of machine-readable data storage media, such as direct access storage (e.g., a conventional "hard drive," redundant array of inexpensive disks (RAID), or another direct access storage device (DASD)), magnetic tape, electronic read-only memory (e.g., ROM, EPROM, or EEPROM), optical storage (e.g., CD-ROM, WORM, DVD, digital optical tape), paper "punch" cards, or other suitable signal-bearing media including transmission media such as digital and analog and communication links and wireless. In an illustrative embodiment of the invention, the machine-readable instructions may comprise software object code, compiled from a language such as "C," etc.

Logic Circuitry

In contrast to the signal-bearing medium discussed above, the method of patient warming may be implemented using logic circuitry, without using a processor to execute instructions. In this embodiment, the logic circuitry is implemented in the controller 104, and serves to perform an operational sequence according to this invention as described below. The logic circuitry may be implemented using many different types of circuitry, as discussed above.

Manual Implementation

As still another option, instead of using logic circuitry, digital data processors, or any other hardware, the controller 104 may be omitted entirely, with these functions being performed manually by medical staff attending to the patient 102.

Patient Warming Sequence

Figure 8:
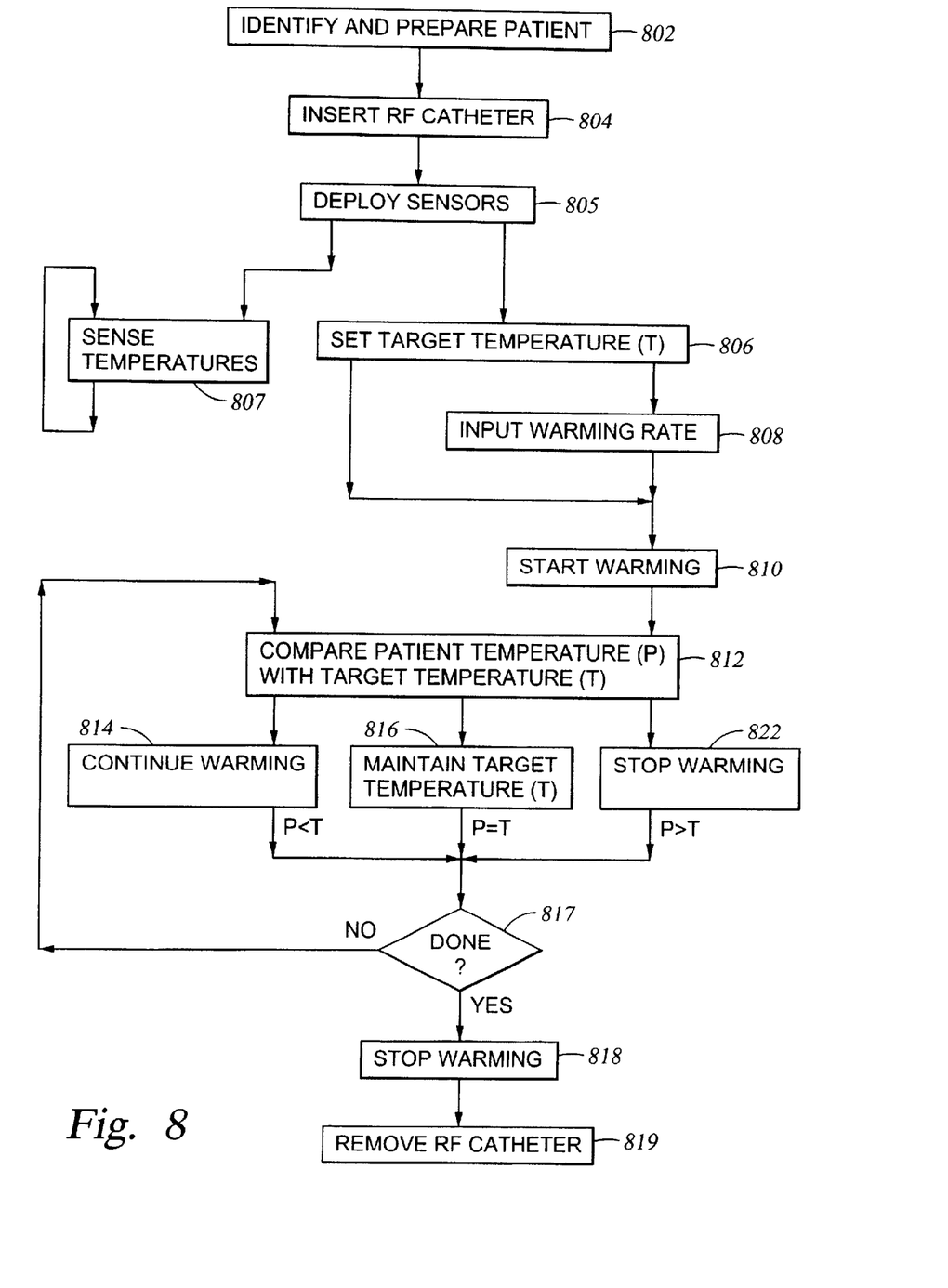
FIG. 8 is a flowchart of an operatiornal sequence for systemic patient warming by dielectric warming of blood, according to the invention.

FIG. 8 shows an operating sequence 800 for patient warming to illustrate one example of the present invention. For ease of explanation, but without any intended limitation, the example of FIG. 8 is described in the context of FIGS. 1–7, as described above. In step 802, medical staff verify the patient's identity and prepare the patient for treatment. As an example, such preparation may involve bathing, shaving, dressing, and like activities.

After step 802, medical staff interconnect the components of the system 100 and deploy the catheter 114 to the appropriate bodily site in step 804. If the system 100 components are pre-assembled, assembly steps may be skipped where possible. Deployment of the catheter 114 includes a number of sub-steps. First, medical staff create an opening for insertion of the catheter 114. For example, medical staff may cut an appropriately located incision or puncture in the neck (for insertion of the catheter into the jugular vein) shoulder/chest (for insertion into the subclavian vein), or groin (for insertion of the catheter into the femoral vein). Then, medical staff feed the catheter 114 into the incision until the emitter structure reaches the desired body cavity. The catheter may be inserted through an introducer sheath (not shown), nozzle, tube, funnel, or another device if desired.

The emitter structure's small cross-sectional size permits a significant amount of blood to flow past the emitter structure within the body cavity. Yet, the emitter's cross-sectional size determines the amount of heating that can be applied without damaging blood or neighboring tissue, since the emitter's size restricts blood flow to some degree and therefore dictates the heating time of blood flowing past the emitter. The emitter structure allows blood to flow around and through the emitter (in the case of "flow-through" embodiments), or just around the emitter (in the case of "flow-around" embodiments). As an example, the emitter may have a cross-sectional diameter of about 5 mm.

In addition, if the catheter 114 is being deployed with the unipolar emitter structure 500 (FIG. 5), step 804 also involves the tasks of medical staff attaching the conductive grounding plate 150 to a suitably conductive area of the patient's skin such as the patient's back, buttocks, etc.

In the case of the structure 410, the sleeve 411 collapses during installation in step 804, ultimately resuming normal shape as permitted by the dimensions of the deployment body cavity. In the case of the structures 430, 440, the spacers are straightened lengthwise during the installation of step 804, and then actuated (or permitted to selfactuate) and create corresponding bights by appropriate use of the sleeve 437 or retractor 443.

In step 805, medical staff deploy the sensors 130, 132. As illustrated, the sensor 130 is installed in the body passage where the catheter 114 is deployed, and serves to detect the temperature of blood heated by the catheter 114. Alternatively, if the sensor 130 is integrated with the emitter structure (such as shown in FIG. 3), the step of deploying the sensor 130 is satisfied when the emitter structure is put in place and blood flow positions the sensor 130 downstream from the emitter structure, a fixed distance away according to the length of the tether 330. The other sensor 132 may be deployed upon the patient 102, at one of many sites known to be accurate for measuring body core temperature. Some examples include esophageal, bladder, rectal, or oral installation.

After step 805, the sensors 130, 132 begin to sense bodily temperature in step 807 and provide respective machine-readable outputs (such as digital or analog signals) to the controller 104. Attentively, instead of sensing temperature directly, the sensors 130,132 may detect another physiological characteristic that is nonetheless indicative of body temperature, such as metabolic rate.

After step 805, step 806 sets a target temperature. The target temperature establishes a temperature goal at the body core sensor 132. The target temperature may be set manually, such as by human operator via the input 102, or the controller 104 may use a predetermined temperature such as thirty-seven degrees Celsius. After step 806, step 808 sets a warming rate. The warming rate, which may be set manually or automatically, comprises a target rate, range, maximum, minimum, average or other specification of a desired rate (such as degrees of temperature per minute) for warming of the patient's core temperature using the indwelling catheter 114. A maximum warming rate may be set, for example, to ensure that the emitter does not generate an excessive amount of heat in an attempt to increase the patient's body temperature at impossible or unsafe rates.

After step 808, warming begins in step 810. Namely, the controller 104 directs the generator 106 to begin generating RF signals, the generator 106 outputs these signals to the emitter structure via the link 112, and the emitter structure responds by radiating electromagnetic energy within the body cavity, causing dielectric heating of blood or other bodily fluids. In the case of the bipolar flow-around emitter 200 (FIG. 2), an electric field is created between the electrodes 208, 210, thereby heating blood that is present around the catheter body 206. In the case of the bipolar flow-around emitter 300, an electric field is created between the electrodes 310, 308, thereby heating blood that is present around the catheter body 306. In the case of the bipolar flow-through emitter 400, an electric field is created between the outer, negative electrode 402 and the inner, positive electrode 404, thereby heating blood that passes through the catheter 400 in the space 406. In the case of the bipolar flow-around emitter 500, an electric field is created between the catheter body 506 and the patient's body (including the vessel 509), thereby heating blood that is present in the space 510 within the blood vessel 509.

The amount of radiation is sufficient to warm blood or bodily fluids present in the cavity yet insufficient to cause necrosis of tissue surrounding the body cavity because of various factors, including the temperature-limited parameters of the electric field setting of the generator 106, such as power, duty cycle, etc. Another factor is the spatial separation of emitter from vessel walls due to structure as shown in FIGS. 4C–4H.

Regarding the settings of the generator 106, the level of heat delivered to the patient is set by establishing a desired level of electrical power applied to the emitter. Power may be increased, for example, by increasing the average amplitude of the electric field, increasing the duty cycle of the electric field's modulation, etc. Heating is conducted so as to avoid clinically significant localized hot spots capable of damaging tissue or blood by protein denaturation. Importantly, this radiation is delivered to the patient's blood as blood flows past the emitter; the patient's circulatory system therefore aids in distributing the warmed blood through the patient's body, resulting in systemic heating. The patient's circulatory system may be aided, if desired, by manual or mechanical blood circulating devices or machines. As discussed below, this application of RF radiation is continued for a sufficient time to affect a desired increase in body core temperature of the patient.

In step 812 the controller 104 compares the patient's temperature (from body core sensor 132) with the target temperature (which was set in step 806). As an alternative to use of the sensor 132, medical staff may sample the patient's core temperature manually, and input this data into the controller 104 using the operator input 108. If the patient's temperature exceeds the target temperature, the controller 104 in step 822 directs the generator 106 to stop warming. If the patient's temperature is less than the target temperature, the controller 104 in step 814 directs the generator 106 to continue warming at the rate designated in step 808. Optionally, in step 814 the controller 104 may direct the controller 106 to increase the rate of warming, if this will not exceed the warming rate of step 808. In general, warming may be increased by increasing the power level delivered from the generator to the emitter, and subsequently, the power absorbed by the blood. An increase in power level may be accomplished by either increasing the electric field amplitude, or, if duty-cycle modulation is being used for average-power control, increasing the modulation duty cycle. In the specialized case where the dielectric loss parameters of bodily fluid are very different between two frequencies, frequency modulation may be used to alter the power absorbed by the blood. In contrast to steps 822/814, if the patient's temperature equals the target temperature, the controller 104 in step 816 directs the generator 106 to maintain the target temperature by decreasing the power, application time, or other parameters.

As an alternative to step 812 as illustrated, step 812 may require a temperature adjustment whenever the patient's core temperature is outside a specific temperature range, such as thirty-five to forty degrees Celsius. As an additional feature, step 812 may trigger step 822 to stop warming whenever blood proximate the sensor 130 exceeds a prescribed maximum temperature, such as forty degrees Celsius, in order to prevent blood damage, tissue necrosis, or other heat induced conditions. As still another example, step 812 may consider a combination of patient core temperature and on-site blood temperature. Step 812 may also seek to perform more complex temperature management functions, such as limiting any body core temperature excursions to a maximum time or temperature, etc. Furthermore, as still another alternative or additional feature, step 812 may activate a visual, tactile, audio, or other sensory alarm if the sensors 130 and/or 132 indicate onset of a dangerous condition. Specific temperature management techniques, such as those discussed above, may be implemented in step 812 by manual action by medical staff and/or automated programming of the controller 104.

After any of steps 814, 816, 822, step 817 asks whether the warming process is finished. This inquiry may be made by the controller 104 (automated) in some cases, or by medical staff (manually) in other cases. Patient warming may terminate, for example, after expiration of an operator-designated time period (such as one hour), when medical staff wish to move the patient, when medical staff wish to perform a procedure that is inconsistent with patient warming, when the patient reaches set temperature, etc.

If the warming process is not finished, step 817 returns to step 812. On the other hand, when warming is finished, the controller 104 directs the generator 106 to stop providing its RF frequency output signal (step 818). In step 819, medical staff remove the catheter 114 and sensors 130, 132. During step 819, features such as expandable spacers (FIGS. 4H–4I) are un-actuated to aid in removing the catheter. Also as part of step 819, the patient's incision is closed and any other applicable post treatment procedures are performed. Step 819 completes the sequence 800.

Determination of Heating Strategy

While not wishing to bound by any particular theory, one school of thought says that operation of the catheter as described above is a manifestation of a principle called dielectric loss, explained as follows. An RF field is an electric field, typically oscillating at a frequency in the range of Megahertz (MHz, millions of cycle per second) to Gigahertz (GHz, billions of cycles per second). When an RF field is applied to a dielectric (non-electrically-conductive) material, the radio waves propagate through the material. If the material contains "polar" molecules, those molecules try to align their poles to the rapidly alternating electric field.

The effect on a dielectric material of having its molecules trying to "follow" the electric field depends on a material-specific characteristic called "dielectric loss." In materials with low dielectric loss, the molecules may follow the field without losing significant energy as they "flip" from one field orientation to the other and back. For a strongly polar and high-dielectric-loss molecule, such as water, the intermolecular "friction" of water molecules rubbing against one another as they try to follow the alternating field creates hysteresis losses and warms the bulk material.

This is similar to the method by which a microwave oven heats foods, and explains the common observation that a microwave oven is good at heating a cup of water to make tea, but bad at heating dry bread (which has low water content and low dielectric loss). The electric field itself is not "hot" per se; it will pass through a dielectric material without losing significant energy and therefore substantially without heating the material. Only when there are dielectric losses in the material through which the field passes will power be absorbed from the electric field and result in heating. This method deposits heat more-or-less uniformly within the bulk of the object, warming "from the inside out."

The nature of the interaction of the electric field with blood flowing more or less parallel to the emitter's longitudinal axis is to create a hollow cylinder (an annulus) of fluid in the zone of influence of the RF field. In general, the heating of any incremental volume of blood can be expressed as the time integral of the field power experienced by the blood over its path through this zone of influence, multiplied by the dielectric loss factor of the blood, divided by the specific heat of the fluid. Since the loss factor and specific heat of the blood are constants, the increase in temperature of an incremental volume of blood is a function of the time integral of the field power it is exposed to over its path through the zone of influence. Blood heating is therefore affected by the magnitude of RF field power and the time of exposure to this field.

As mentioned above, the emitter is responsible for creating a local circularly symmetric and longitudinally uniform RF electric field. The field's interaction with liquid blood in the blood vessel results principally from dielectric losses in the water component of the blood, creating distributed heating.

The RF field's interaction with the nearby blood creates a heat input to the circulatory system directly in the large vessels, where the warmed blood can be put to the most effective use in raising the patient's core temperature. For a numerical example, a vessel diameter of 13 mm is assumed for the superior vena cava (in which the catheter resides), a diameter of 5 mm for the body of the catheter 114, a flow rate of two liters per minute of blood through the vessel, a 2 mm effective radial absorption depth for the RF energy surrounding emitter, 35° C. blood present at the upstream end of the catheter, and a 40° C. limit to the allowable blood temperature at the downstream end of the catheter.

The internal area of the vena cava is 1.33 $cm^2$. Subtracting the flow area occluded by the 5 mm diameter catheter, which is 0.2 $cm^2$ leaves a net flow area of 1.13 $cm^2$. Dividing the flow rate by the effective cross-section area, produces a mean fluid velocity of 29.5 cm/second.

For a 2 mm radial absorption depth with a 5 mm diameter catheter, the effective annular area of the RF field is 0.44 $cm^2$. Given the blood's flow velocity of 29.5 cm/sec, 13 $cm^3$ of blood flows through the annulus in one second. At a specific heat estimated at 1.0, it takes 4.187 Joules of energy (one calorie) to raise the temperature of 1 $cm^3$ of blood by one degree Celsius. Since 13 $cm^3$ per second of blood passes through the annulus, and a 5° C. temperature rise in the blood occurs as it transits the annulus, a power load of 272 Watts may be introduced into the blood by dielectric heating in this example. Accordingly, the controller 104 directs the generator 106 appropriately to limit the maximum power to 275 Watts.

This is far more power than can be transferred to the patient by contact-type heating, either with a heated-surface indwelling catheter, or other means external to the body. The invention's superior ability to deliver clinically significant power levels can be summed up as follows: RF power is distributed through a volume of blood, allowing higher gross power loadings with lower local heating than would be possible with a surface-transfer method of exchanging thermal energy.

By contrast, a catheter comprising a heated cylindrical surface on the order of 5 mm diameter and with a wetted area of approximately 1.9 $cm^2$, held at a temperature near 40° C., will transfer only about 10 watts into 35° C. blood flowing along it axially. Furthermore, the catheter surface could not be heated much above 43° C. as a means of increasing the heat transfer rate, as this approaches the protein denaturation temperature, at which irreversible damage will occur to the blood. From this example, it can be seen that surface-transfer methods of exchanging thermal energy directly into the blood are limited to an order of magnitude less input power than the present invention's dielectric heating method.

OTHER EMBODIMENTS

While the foregoing disclosure shows a number of illustrative embodiments of the invention, it will be apparent to those skilled in the art that various changes and modifications can be made herein without departing from the scope of the invention as defined by the appended claims. Furthermore, although elements of the invention may be described or claimed in the singular, the plural is contemplated unless limitation to the singular is explicitly stated. Additionally, ordinarily skilled artisans will recognize that operational sequences must be set forth in some specific order for the purpose of explanation and claiming, but the present invention contemplates various changes beyond such specific order.

What is claimed is:

1. A patient warming method, comprising operation of:

providing a flow-through emitter wherein the emitter comprises an elongated inner electrode residing within and substantially coaxial to a hollow, elongated outer electrode;

utilizing a catheter to position the flow-through emitter within a body cavity of a patient;

the emitter structure allowing bodily fluids within the body cavity to flow through the emitter;

during the flow of bodily fluids through the emitter, operating the emitter to radiate electromagnetic energy sufficient to warm the fluids flowing through the emitters.

2. A patient warming method, comprising operations of:

providing a flow-through emitter structure comprising an elongated inner electrode residing within and substantially coaxial to a hollow, elongated outer electrode;

utilizing a catheter to position the flow-through emitter structure within a body cavity of a patient;

the emitter structure permitting bodily fluids to pass between the inner and outer electrodes;

during passage of bodily fluids through the emitter, operating the emitter to radiate electromagnetic energy sufficient to warm the bodily fluids.

3. A patient warming method, comprising operations of:

utilizing a catheter to position a multi-polar emitter structure within a blood-bearing body cavity of a patient, wherein the blood flows past the emitter, during the flow of blood past the emitter, operating the emitter to create an electromagnetic field between the multiple poles sufficient to warm blood present in the cavity; and continuing radiation of electromagnetic energy to achieve a selected increase in body core temperature of the patient through the warming of blood.

4. The method of claim 3, where the operation of utilizing a catheter to position a multi-polar emitter structure within a selected blood-bearing body cavity of a patient comprises:

positioning an elongated emitter structure comprising an elongated emitter body and multiple electrodes spiraling about the emitter body in substantially parallel paths.

5. A patient warming method, comprising operation of:

providing an emitter structure comprising an elongated emitter body and multiple electrodes spiraling about the emitter body in substantially parallel paths;

utilizing a catheter to position the emitter structure within a patient's body cavity such that the emitter structure is immersed in bodily fluid;

creating an electromagnetic field between the electrodes sufficient to warm bodily fluid surrounding the emitter structure.

6. A patient warming method, comprising operations of:
providing an elongated emitter, including one or more electrodes and also including fluid permeable spacing structure situated about the emitter;
utilizing a catheter to position the emitter within a body cavity of a patient;
operating the electrodes to radiate electromagnetic energy sufficient to bodily fluids present in the cavity; and
while the emitter structure is positioned within the body cavity, the spacing structure resiliently separating the electrodes from walls of the body cavity while permitting bodily fluids to pass through the spacing structure.

7. The method of claim 6, where:
the operation of providing a spacing structure comprising providing resilient spacers attached to the emitter body;
the separating operation comprising the resilient spacers exerting pressure outward from the electrodes against walls of the body cavity.

8. The method of claim 6, where:
the operation of providing an emitter comprising providing an emitter body including resilient spacers attached to the emitter body, the spacers comprising wires each having a proximal end attached to the emitter body and a distal end projecting form the emitter body at an acute angle with respect to a longitudinal axis of the emitter body;
the operation of providing separation comprising the wires distancing the emitter body from walls of a body cavity while the emitter structure is positioned within the body cavity.

9. The method of claim 6, where:
the operation of providing an emitter comprising providing an emitter body including resilient spacers attached to the emitter body, the spacers comprising wires each having a proximal end attached to the emitter body and a distal end projecting from the emitter body at an acute angle with respect to a longitudinal axis of the emitter body, the emitter body and spacers being surrounded by a collapsible sheath;
the operation of providing separation comprising the wires distancing the emitter body from the sheath.

10. The method of claim 6, where:
the operation of providing an emitter comprising:
providing an elongated emitter body having a proximal end and also having an opposing, distal end, the emitter body including one or more electrodes operable to radiate electromagnetic energy;
provides multiple resilient spacers each coupled to a distal mount at the emitter body's distal end and also coupled to a proximal mount longitudinally disposed from the distal end, where at least one of the distal mount and proximal mount are longitudinally movable along the emitter body;
provides remote actuator coupled to at least one of the distal and proximal mounts;
the separating operation comprising operating the remote actuator to move at least one of the distal and proximal mounts longitudinally along the emitter body in order to slacken the spacers to create bights therein.

11. A catheter apparatus, comprising:
an elongated catheter having a distal end;
an elongated emitter structure having a proximal end attached to the catheter and also an opposing, distal end, the emitter structure including one or more electrodes;
a blood temperature sensor;
a tether flexibly coupling the temperature sensor to the emitter structure's distal end to suspend the sensor downstream of the emitter structure under influence of blood flow in the cavity.

12. A catheter apparatus, comprising:
an elongated catheter having a distal end;
an elongated emitter structure having a proximal end attached to the catheter and also an opposing, distal end, the emitter structure including one or more electrodes;
a blood temperature sensor;
means for coupling the temperature sensor to the emitter structure's distal end to suspend the sensor downstream of the emitter structure under influence of blood flow in the cavity.

13. A catheter apparatus, comprising:
an elongated catheter having a distal end;
an elongated emitter structure having a proximal end attached to the catheter's distal end and also an opposing, distal end, the emitter structure comprising:
a hollow elongated outer electrode;
an elongated inner electrode;
one or more spacers positioning the inner electrode within and substantially coaxial with the outer electrode to define a blood flow path between inner and outer electrodes.

14. A catheter apparatus, comprising:
an elongated catheter having a distal end;
an elongated emitter structure having a proximal end attached to the catheter's distal end and also an opposing, distal end, the emitter structure comprising:
a hollow elongated outer electrode;
an elongated inner electrode;
means for positioning the inner electrode within an substantially coaxial with the outer electrode to define a blood flow path between inner and outer electrodes.

15. A patient warming method, comprising operations of:
utilizing a catheter to position an emitter within a blood-bearing body cavity of a patient, the emitter including a tether coupling a temperature sensor to a distal end of the emitter,
wherein the blood flows past the emitter, the tether suspending the temperature sensor downstream of the emitter in the body cavity under influence of blood flow in the cavity;
during the flow of blood past the emitter, operating the emitter to radiate electromagnetic energy sufficient to warm blood present in the cavity; and
operating the temperature sensor to sense temperature of blood within the body cavity.

16. A catheter apparatus, comprising:
an elongated catheter having a distal end;
an elongated emitter structure having a proximal end attached to the catheter and also an opposing, distal end, the emitter body including one or more electrodes operable to radiate electromagnetic energy;
a fluid permeable spacing structure attached to the emitter body to resiliently distance the emitter structure from walls of a body cavity while the emitter structure is positioned within the body cavity, wherein the spacing structure comprises multiple wires each having a proximal end attached to the emitter body and a distal end projecting from the emitter body at an acute angle with respect to a longitudinal axis of the emitter body.

17. The apparatus of claim 16, further comprising:
balls attached to the wires' distal ends.

18. The apparatus of claim 16, further comprising: pads attached to the wires' distal ends.

19. The apparatus of claim 16, the wires forming a rounded loop at their distal ends.

20. The apparatus of claim 16, further comprising:
a collapsible sheath surrounding the emitter body and spacing structure.

21. A catheter apparatus, comprising:
an elongated catheter having a distal end;
an elongated emitter body having a proximal end attached to the catheter's distal end and also having an opposing, distal end, the emitter body including one or more electrodes operable to radiate electromagnetic energy;
multiple resilient spacers each coupled to a distal mount at the emitter body's distal end and also coupled to a proximal mount longitudinally disposed from the distal end;
at least one of the distal mount and proximal mount being longitudinally movable along the emitter body;
a remote actuator operable to move at least one of the distal and proximal mounts longitudinally along the emitter body to selectively slacken the spacers to create bights therein.

22. The apparatus of claim 21, the distal mount comprising a tip surrounding the emitter body's distal end.

23. The apparatus of claim 21, the proximal mount comprising a ring surrounding the emitter body.

24. The apparatus of claim 21, the distal mount being fixed and the proximal mount being movable, the remote actuator comprising an activating line coupled to the proximal mount.

25. The apparatus of claim 21, the proximal mount being fixed and the distal mount being movable, the remote actuator comprising an activating line coupled to the distal mount.

26. The apparatus of claim 21, further comprising:
a resilient coupling between the distal mount and the emitter body urging the distal mount outward from the emitter body.

27. The apparatus of claim 21, further comprising:
a resilient coupling between the proximal mount and the emitter body urging the proximal mount proximally upon the emitter body.

28. A catheter apparatus, comprising:
an elongated catheter having a distal end;
an elongated emitter body having a proximal end attached to the catheter's distal end and also having an opposing, distal end, the emitter body including one or more electrodes operable to radiate electromagnetic energy;
multiple resilient spacers each coupled to a distal mount at the emitter body's distal end and also coupled to a proximal mount longitudinally disposed from the distal end;
at least one of the distal mount and proximal mount being longitudinally movable along the emitter body;
remotely actuated means for selectively slackening the spacers to create spacing bights therein by moving at least one of the distal and proximal mounts longitudinally along the emitter body.

* * * * *